US009510874B2

(12) United States Patent
Krüger

(10) Patent No.: US 9,510,874 B2
(45) Date of Patent: Dec. 6, 2016

(54) MEDICAL INSTRUMENT FOR HOLDING AND HANDLING A SURGICAL SECURING ELEMENT, AND VERTEBRAL COLUMN STABILIZATION SYSTEM

(71) Applicant: Aesculap AG, Tuttlingen (DE)

(72) Inventor: Sven Krüger, Trossingen (DE)

(73) Assignee: Aesculap AG (DE)

( * ) Notice: Subject to any disclaimer, the term of this patent is extended or adjusted under 35 U.S.C. 154(b) by 113 days.

(21) Appl. No.: 14/447,959

(22) Filed: Jul. 31, 2014

(65) Prior Publication Data

US 2015/0039035 A1 Feb. 5, 2015

(30) Foreign Application Priority Data

Aug. 2, 2013 (DE) .................... 10 2013 108 362

(51) Int. Cl.
*A61B 17/70* (2006.01)
(52) U.S. Cl.
CPC ......... *A61B 17/7082* (2013.01); *A61B 17/708* (2013.01); *A61B 17/7037* (2013.01); *A61B 17/7076* (2013.01); *A61B 17/7085* (2013.01); *A61B 17/7091* (2013.01)
(58) Field of Classification Search
CPC ............ A61B 17/7082; A61B 17/7037; A61B 17/7076; A61B 17/708; A61B 17/7085; A61B 17/7091
USPC .......................... 606/86 A, 279, 104, 99, 914
See application file for complete search history.

(56) References Cited

U.S. PATENT DOCUMENTS

| 8,167,887 | B2 | 5/2012 | McLean |
| 8,211,110 | B1 | 7/2012 | Corin et al. |
| 8,439,922 | B1 * | 5/2013 | Arnold ............... A61B 17/7086 606/104 |
| 2006/0200132 | A1 | 9/2006 | Chao et al. |
| 2008/0275456 | A1 | 11/2008 | Vonwiller et al. |
| 2009/0171391 | A1 | 7/2009 | Hutton et al. |
| 2009/0182382 | A1 | 7/2009 | Justis et al. |
| 2011/0060374 | A1 | 3/2011 | Sicvol et al. |
| 2011/0166606 | A1 | 7/2011 | Stihl et al. |
| 2011/0263945 | A1 | 10/2011 | Peterson et al. |

FOREIGN PATENT DOCUMENTS

DE 202011051211 U1 1/2012

* cited by examiner

*Primary Examiner* — Pedro Philogene
*Assistant Examiner* — David C Comstock
(74) *Attorney, Agent, or Firm* — RatnerPrestia

(57) ABSTRACT

A medical instrument for holding and handling a surgical securing element has a proximal and a distal end. The surgical securing element includes a securing part and a holding part, and is assembled such that in an assembled disposition, the holding part for a connection element is movable in relation to the securing part. The instrument defines a longitudinal axis and includes a pulling part and, movable in relation to the latter in the direction of the longitudinal axis, a pushing part. The proximal end is temporarily couplable to the securing element in the assembled disposition. The instrument further includes an uncoupling device for actively transferring the instrument from a coupled position, in which the pulling part and the holding part are coupled, to an uncoupled position, in which the pulling part and the holding part are separable from one another.

18 Claims, 12 Drawing Sheets

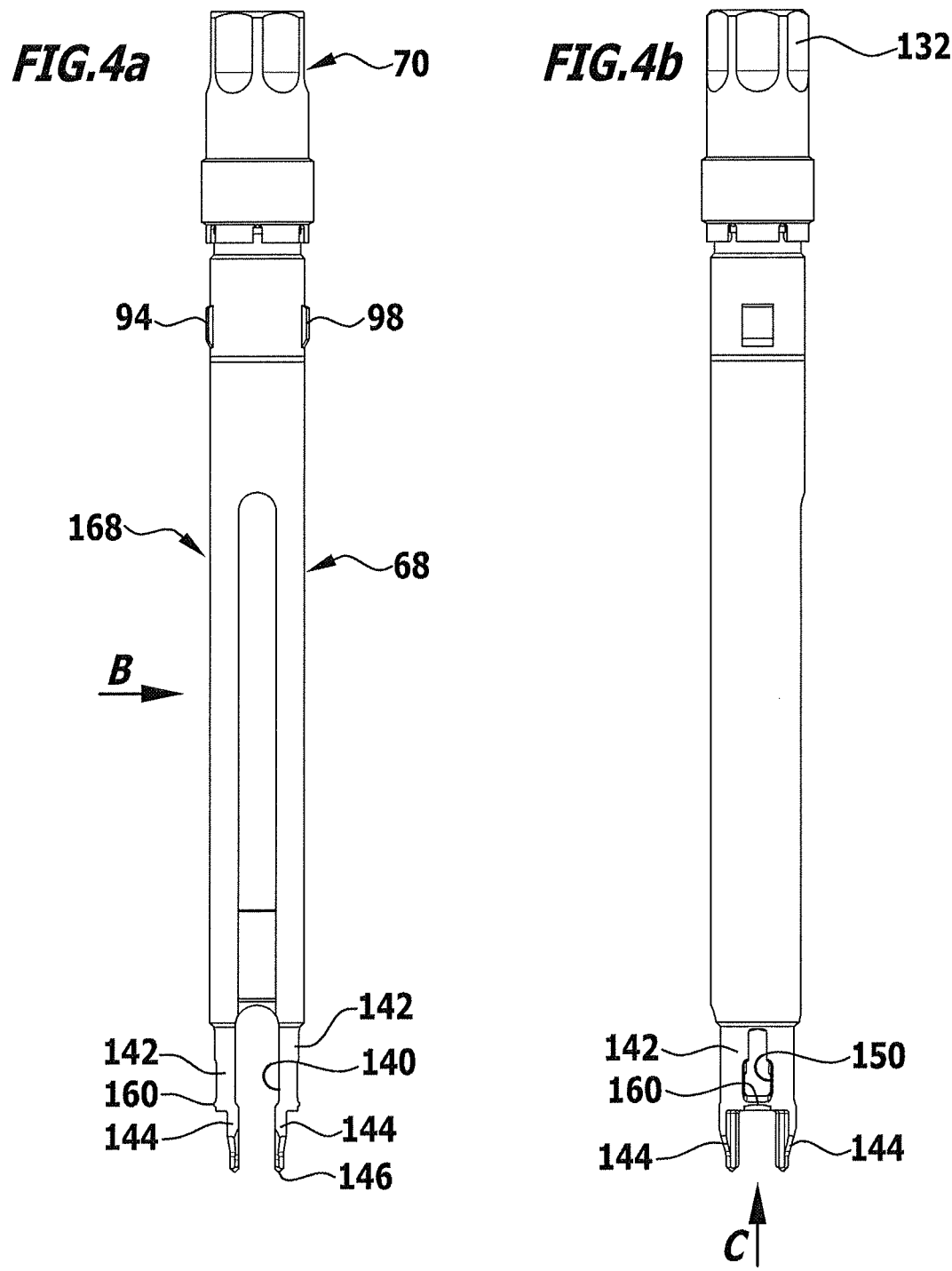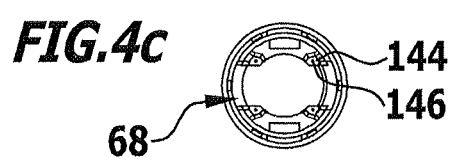

MEDICAL INSTRUMENT FOR HOLDING AND HANDLING A SURGICAL SECURING ELEMENT, AND VERTEBRAL COLUMN STABILIZATION SYSTEM

CROSS-REFERENCE TO RELATED APPLICATIONS

This application claims the benefit of priority of German patent application number 10 2013 108 362.5, filed Aug. 2, 2013, the content of which is incorporated by reference herein in its entirety and for all purposes.

FIELD OF THE INVENTION

The present invention relates to medical instruments for holding and handling a surgical securing element generally, and more specifically to a medical instrument for holding and handling a surgical securing element, which comprises a securing part and a holding part, which is assembled such that in an assembled disposition it is movable in relation to the securing part, for a connection element, wherein the instrument has a proximal and a distal end, defines a longitudinal axis and comprises a pulling part and, movable in relation to the latter in the direction of the longitudinal axis, a pushing part, wherein the proximal end is temporarily couplable to the securing part in the assembled disposition.

Further, the present invention relates to vertebral column stabilization systems generally, and more specifically to a vertebral column stabilization system comprising at least two surgical securing elements and at least one connection element, wherein at least one of the at least two surgical securing elements comprises a securing part, a holding part with a connection element seating, and a fixing element which is fixable to the holding part, for fixing the connection element in the connection element seating.

BACKGROUND OF THE INVENTION

Medical instruments and vertebral column stabilization systems of the type described at the outset are known for example from DE 20 2011 051 211 U1. Like the medical instrument known from U.S. Pat. No. 8,211,110 B1, the instrument described in DE 20 2011 051 211 U1 is coupled by snap-fitting its proximal end, that facing the patient, onto the holding part of the securing element, which may in particular take the form of a forked head that is assembled polyaxially on the securing part.

Snap-fitting the instrument onto the holding part of the securing element can typically be performed simply and reliably. However, it is frequently problematic to release the instrument once the securing element has been put in its final position in a bone part of a patient, for example in a pedicle of the patient.

SUMMARY OF THE INVENTION

In a first aspect of the invention, a medical instrument is provided for holding and handling a surgical securing element. The surgical securing element comprises a securing part and a holding part and is assembled such that in an assembled disposition the holding part for a connection element is movable in relation to the securing part. The instrument has a proximal and a distal end, defines a longitudinal axis and comprises a pulling part and, movable in relation to the latter in the direction of the longitudinal axis, a pushing part. The proximal end is temporarily couplable to the securing element in the assembled disposition. The instrument further comprises an uncoupling device for actively transferring the instrument from a coupled position, in which the pulling part and the holding part are coupled, to an uncoupled position, in which the pulling part and the holding part are separable from one another.

In a second aspect of the invention, a vertebral column stabilization system comprises at least two surgical securing elements and at least one connection element. At least one of the at least two surgical securing elements comprises a securing part, a holding part with a connection element seating, and a fixing element which is fixable to the holding part, for fixing the connection element in the connection element seating. The system further comprises a medical instrument for holding and handling at least one of the surgical securing elements. The at least one of the at least two surgical securing elements is assembled such that in an assembled disposition the holding part for a connection element is movable in relation to the securing part. The instrument has a proximal and a distal end, defines a longitudinal axis and comprises a pulling part and, movable in relation to the latter in the direction of the longitudinal axis, a pushing part. The proximal end is temporarily couplable to the securing element in the assembled disposition. The instrument further comprises an uncoupling device for actively transferring the instrument from a coupled position, in which the pulling part and the holding part are coupled, to an uncoupled position, in which the pulling part and the holding part are separable from one another.

BRIEF DESCRIPTION OF THE DRAWING FIGURES

The foregoing summary and the following description may be better understood in conjunction with the drawing figures, of which:

FIG. 3b shows a sectional view along the line 3b-3b in FIG. 3a;

FIG. 4a shows a side view of the pushing part of the instrument illustrated in FIG. 2;

FIG. 4b shows a side view of the pushing part in the direction of the arrow B in FIG. 4a;

FIG. 4c shows a view of the pushing part in the direction of the arrow C in FIG. 4b;

FIG. 5b shows a view in the direction of the arrow D in FIG. 5a;

DETAILED DESCRIPTION OF THE INVENTION

Figure 1:
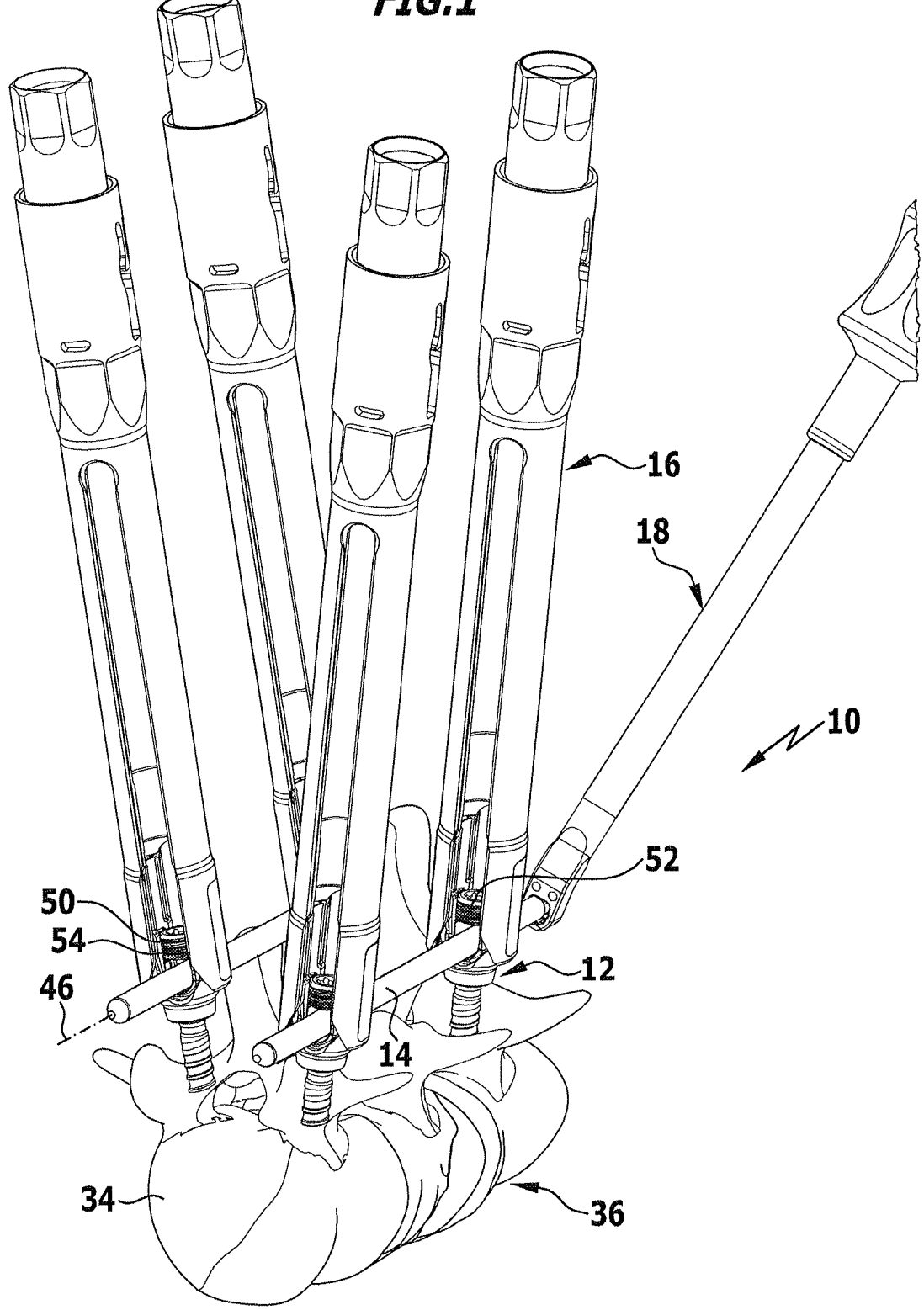
FIG. 1 shows a schematic overall view of a vertebral column stabilization system during implantation.
Figure 2:
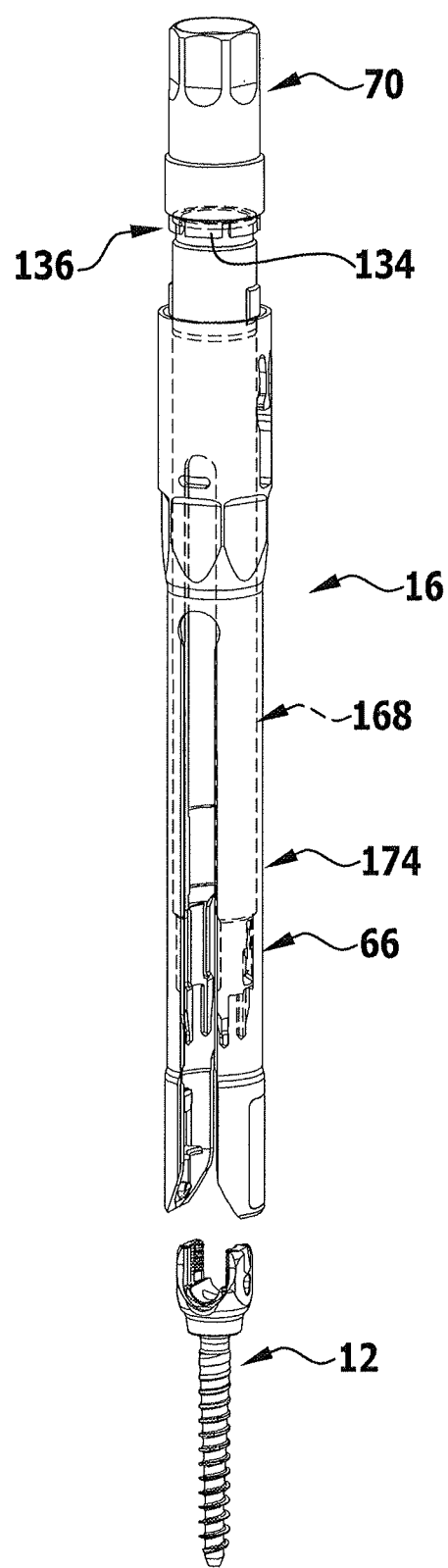
FIG. 2 shows a perspective overall view, partly cut away, of a medical instrument during mounting thereof.
Figure 3A:
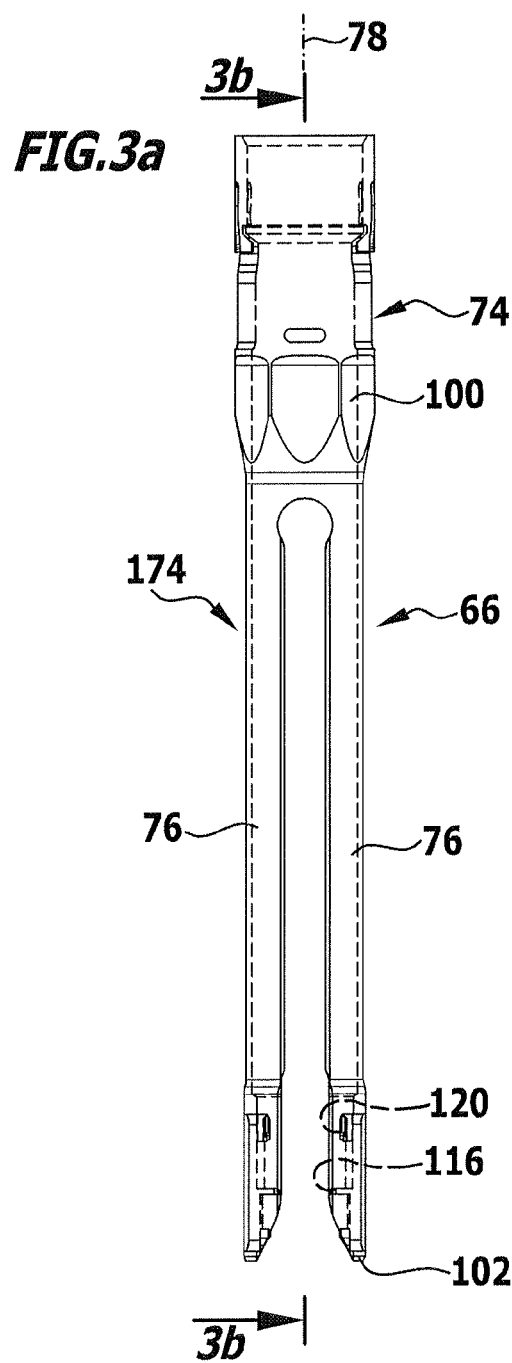
FIG. 3a shows a side view of the pulling part of the instrument illustrated in FIG. 2.
Figure 3B:
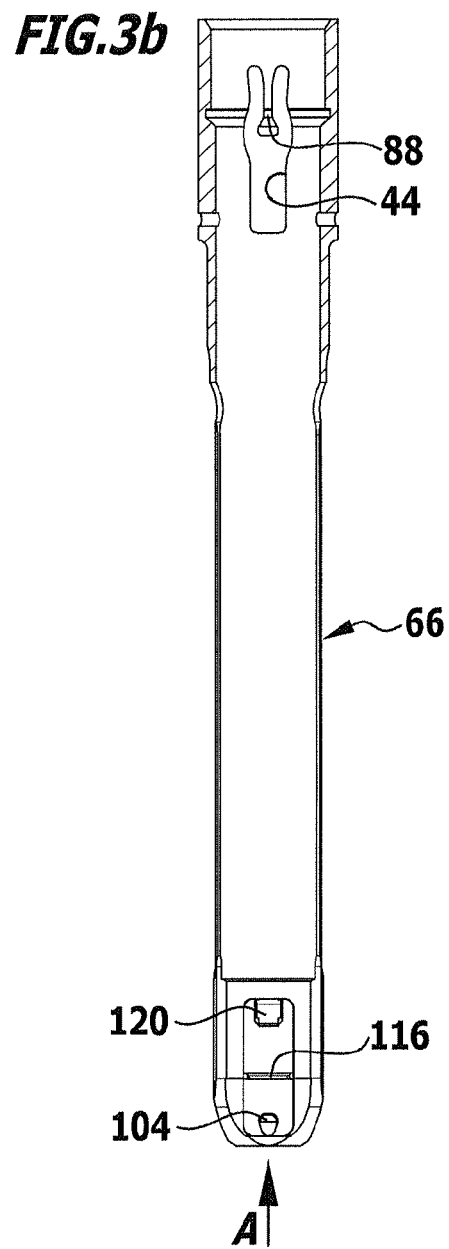
Figure 3C:
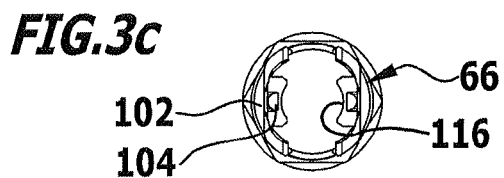
FIG. 3c shows a view in the direction of the arrow A in FIG. 3b.
Figure 5A:
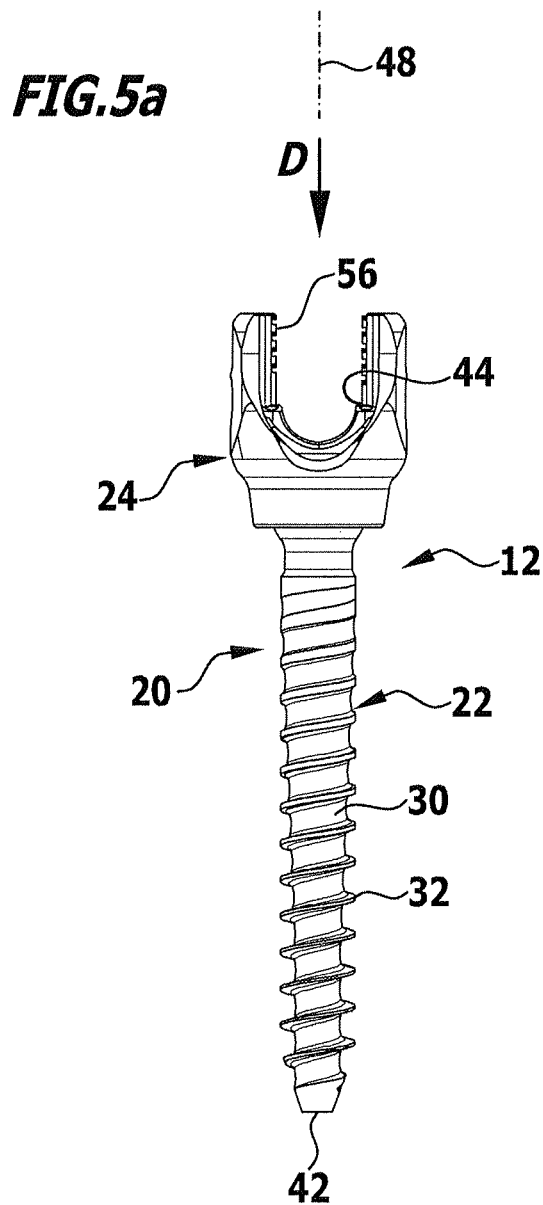
FIG. 5a shows a side view of a securing element with holding part and, movable relative to the latter in the assembled disposition, securing part.
Figure 5B:
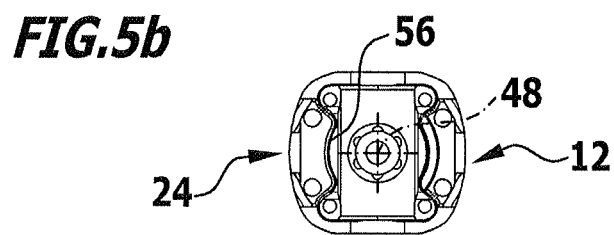
Figure 6:
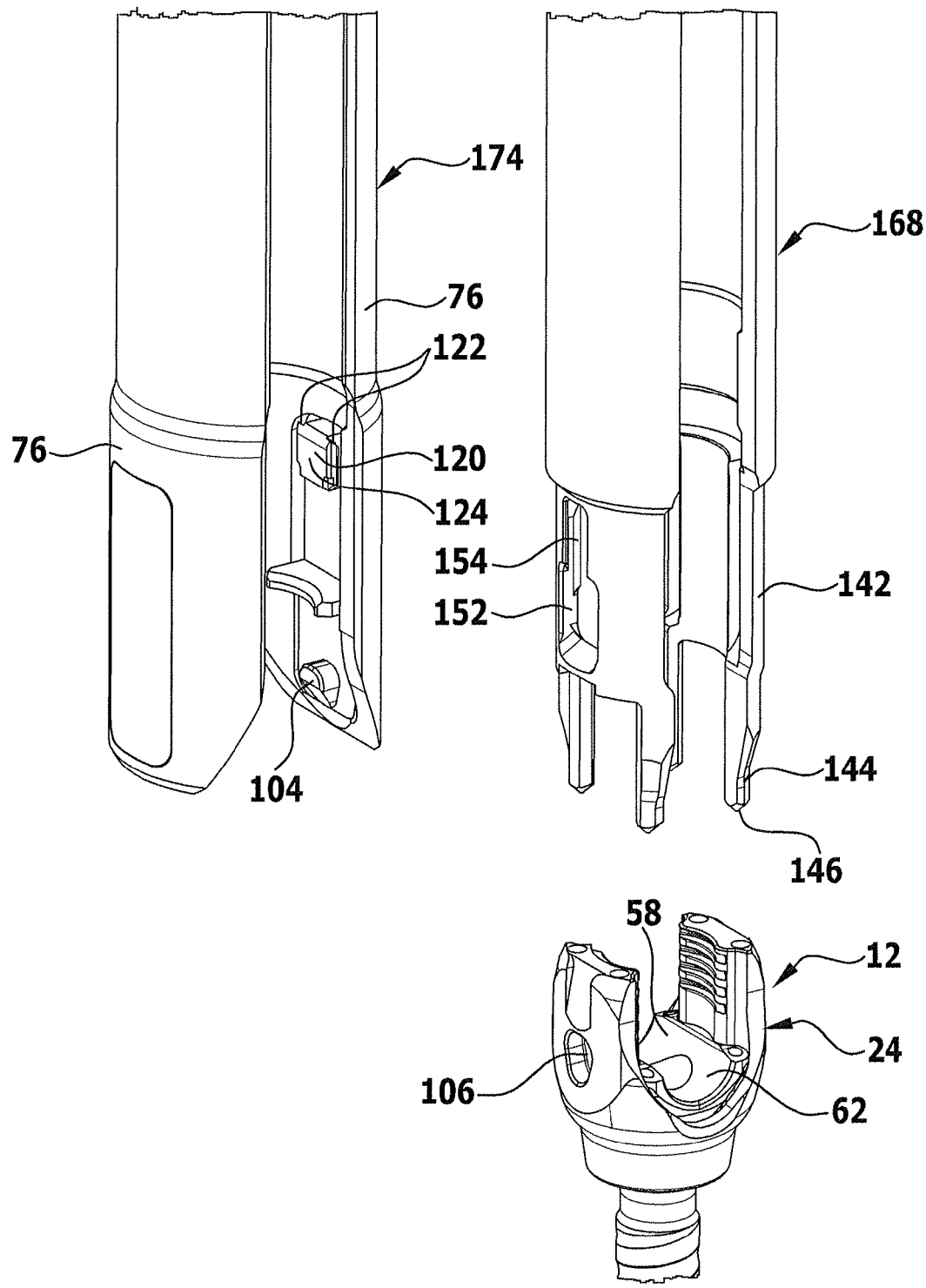
FIG. 6 shows an enlarged view of proximal ends of the pulling part (left) and the pushing part (right) and a distal end of the securing element (bottom)
Figure 7:
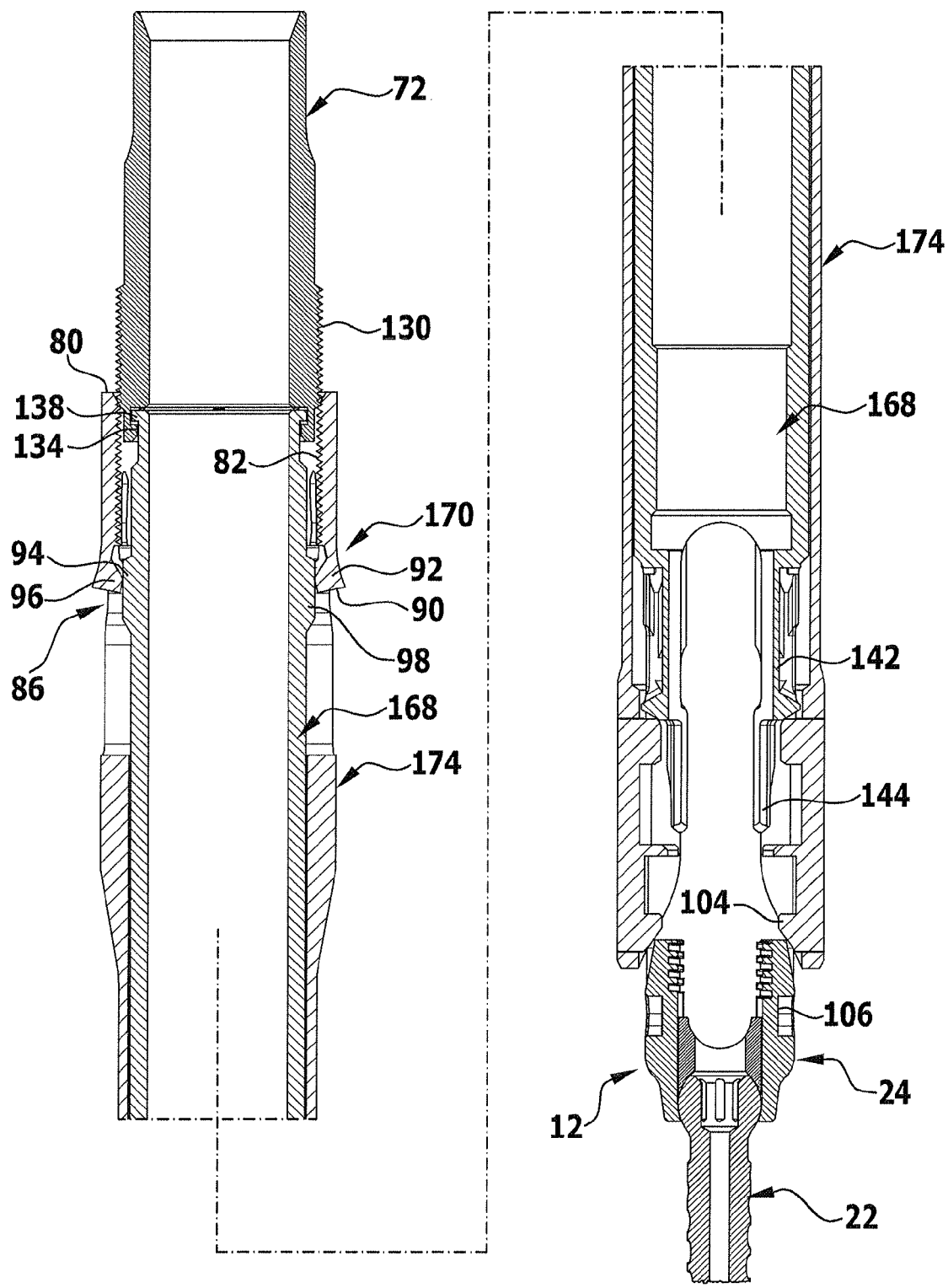
FIG. 7 shows a longitudinal sectional view of the instrument when the pushing part and pulling part are joined and when the instrument is set on a securing element.
Figure 8:
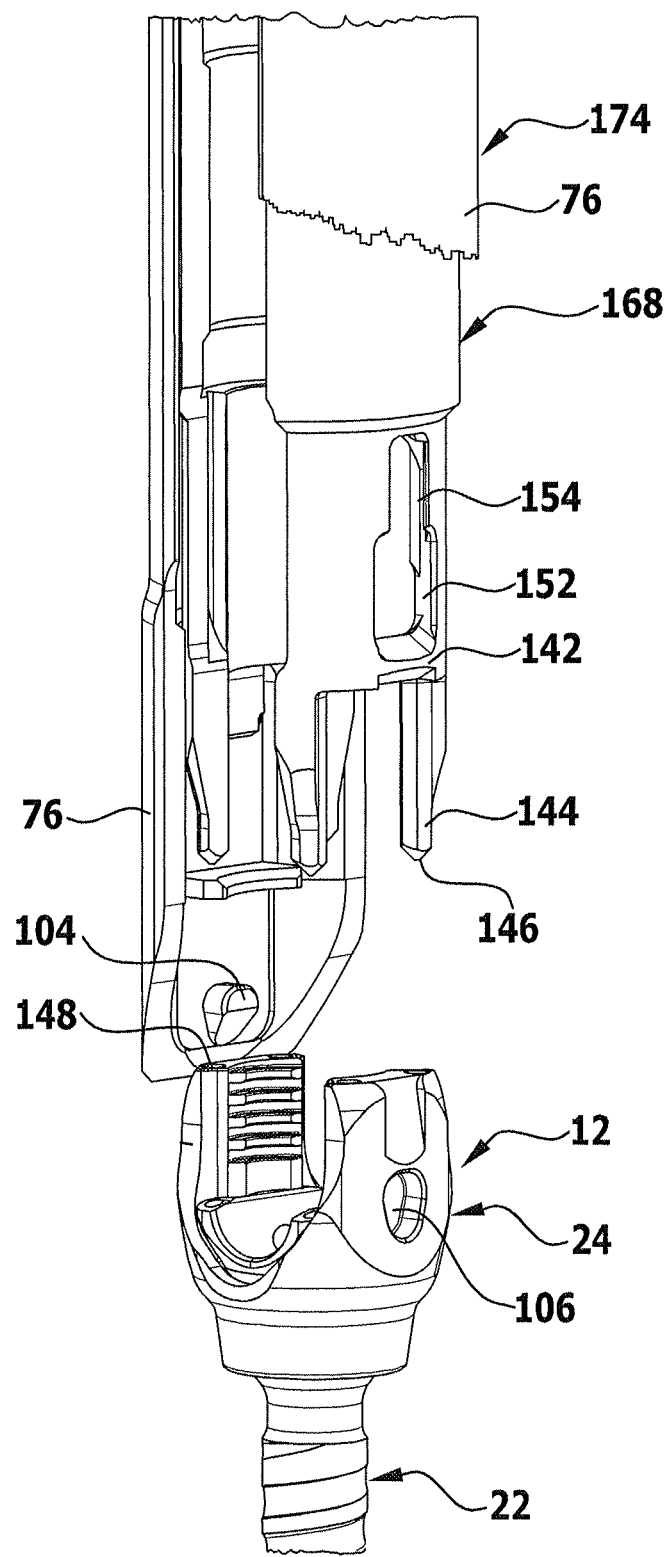
FIG. 8 shows a perspective view, partly cut away, of the right-hand part of the arrangement in FIG. 7.
Figure 9:
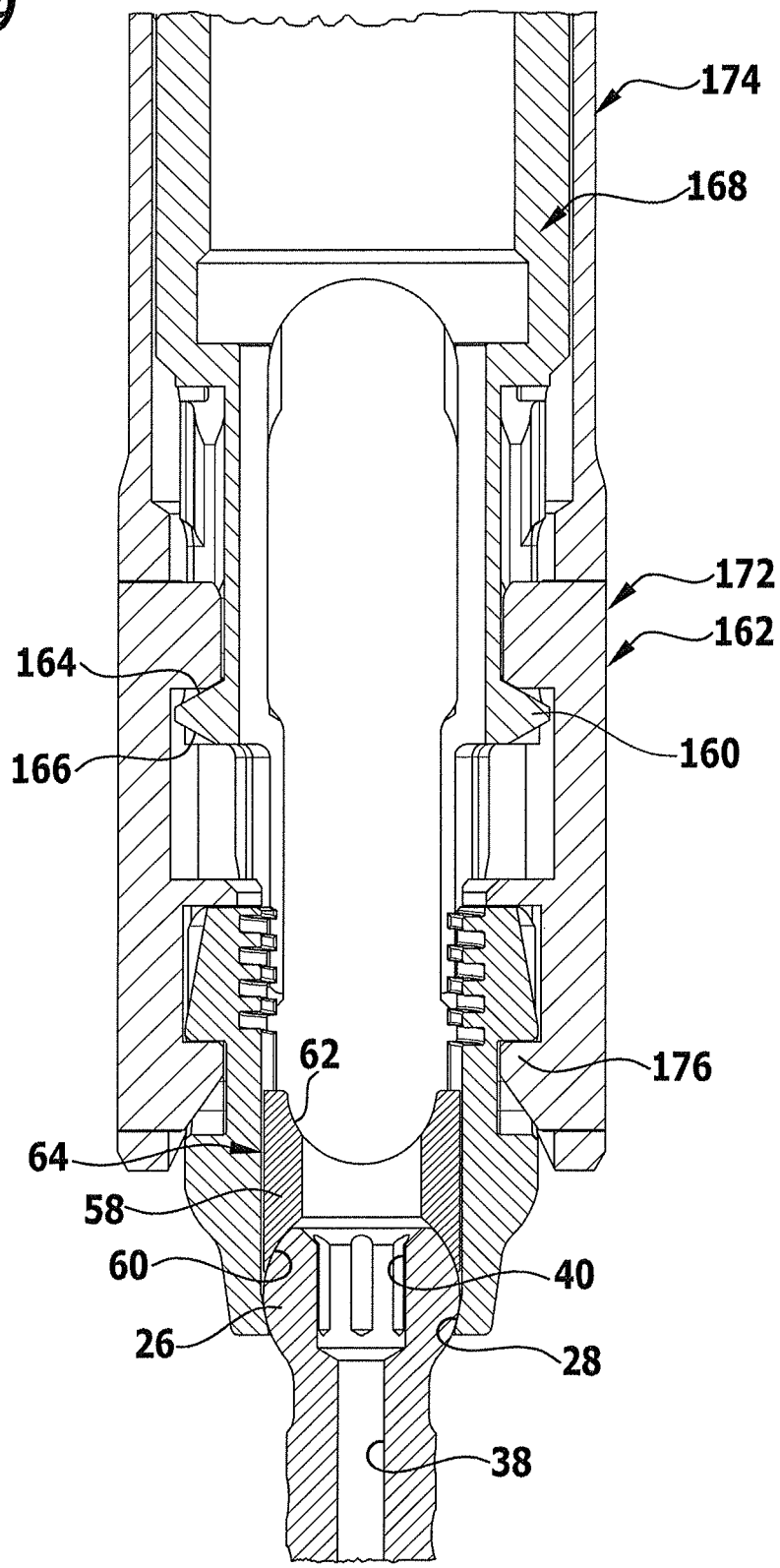
FIG. 9 shows a sectional view of the instrument coupled to the securing element, in the coupled position and unsecured position, wherein the securing element adopts the assembled disposition.
Figure 10:
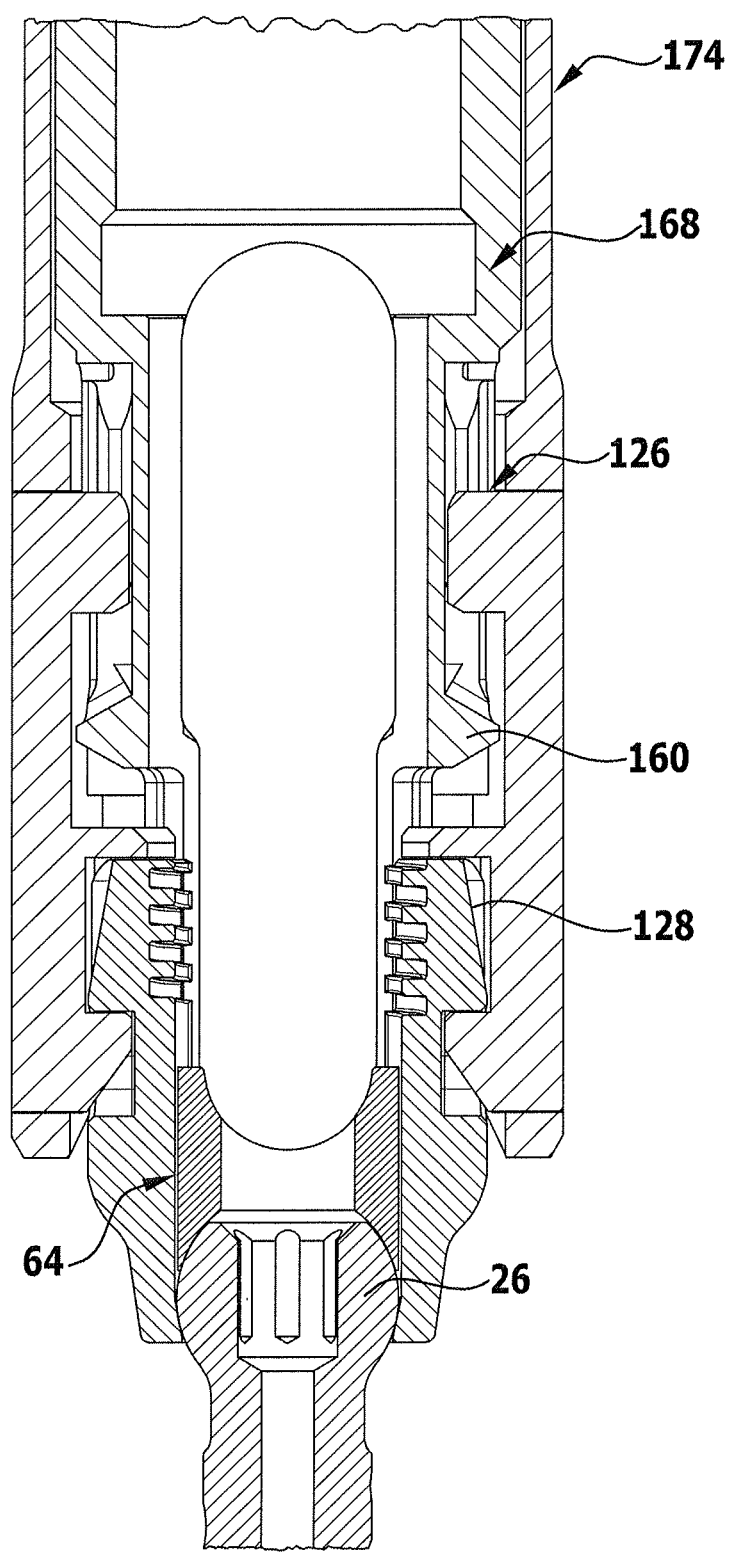
FIG. 10 shows a view similar to FIG. 9, wherein the instrument adopts the secured position.
Figure 11:
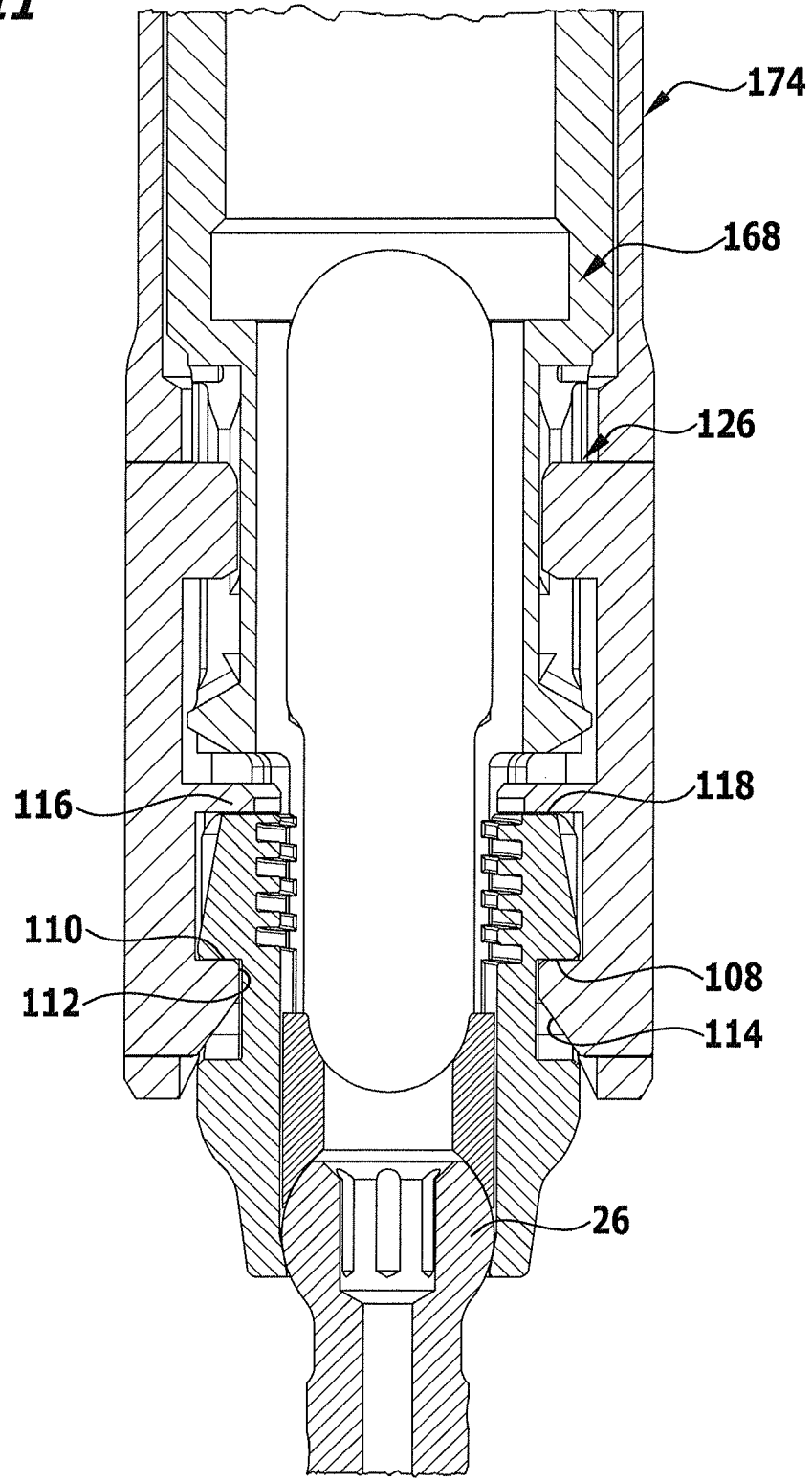
FIG. 11 shows a view similar to FIG. 10, wherein the instrument adopts the locked position, in which the pushing part exerts pushing on a clamping member of the securing element.
Figure 12:
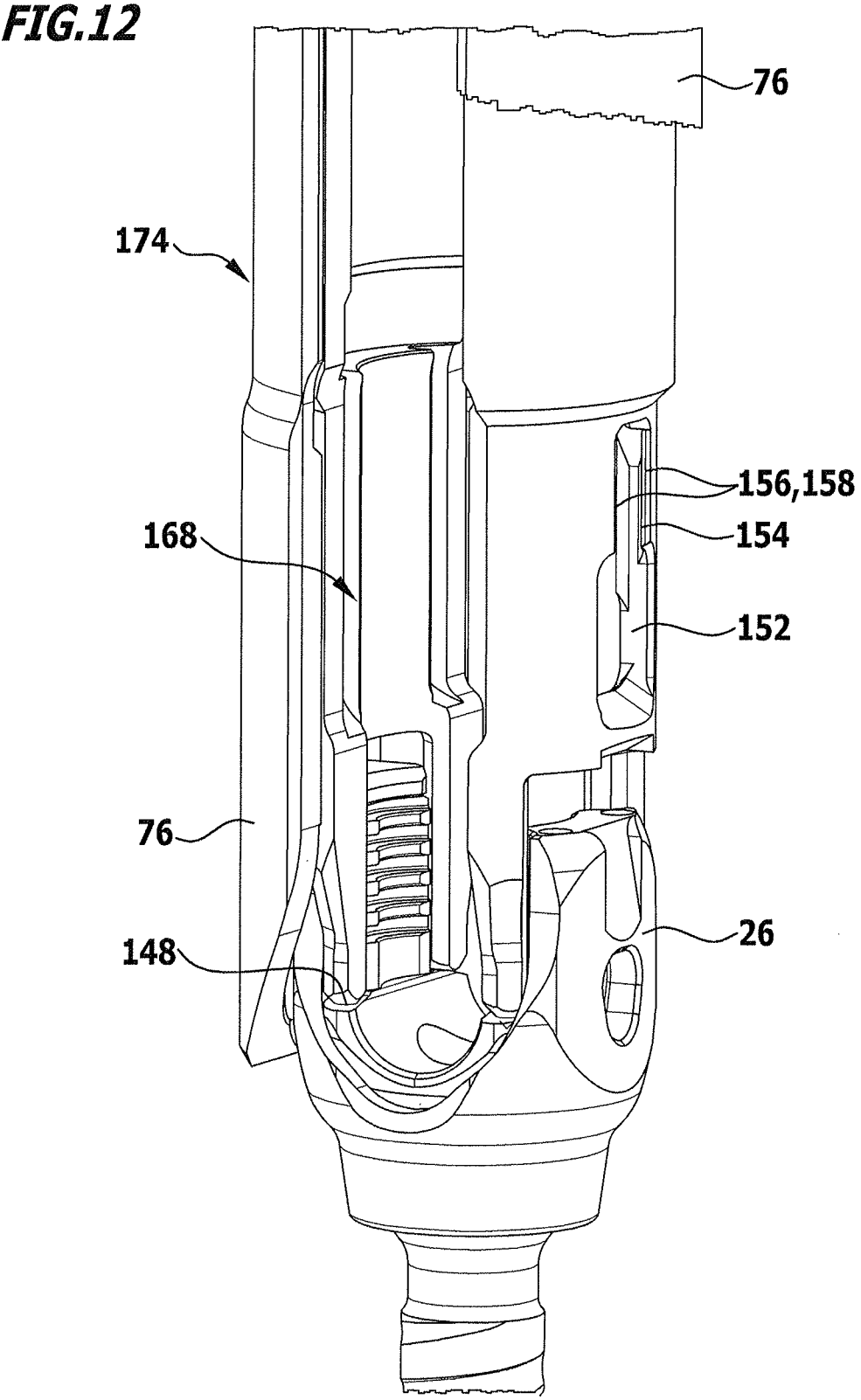
FIG. 12 shows a perspective view, partly cut away, of the arrangement in FIG. 11 in the locked position.

Although the invention is illustrated and described herein with reference to specific embodiments, the invention is not intended to be limited to the details shown. Rather, various modifications may be made in the details within the scope and range of equivalents of the claims and without departing from the invention.

The present invention relates to a medical instrument for holding and handling a surgical securing element, which comprises a securing part and a holding part, which is assembled such that in an assembled disposition it is movable in relation to the securing part, for a connection element, wherein the instrument has a proximal and a distal end, defines a longitudinal axis and comprises a pulling part and, movable in relation to the latter in the direction of the longitudinal axis, a pushing part, wherein the proximal end is temporarily couplable to the securing element in the assembled disposition, further comprising an uncoupling device for actively transferring the instrument from a coupled position, in which the pulling part and the holding part are coupled, to an uncoupled position, in which the pulling part and the holding part are separable from one another.

The further development that is proposed according to the invention in particular enables the medical instrument to be separated from the securing element in a simple and reliable manner. For example, it is possible to construct the uncoupling device such that the instrument may be transferred from the coupled position to the uncoupled position without exerting forces on the holding part. In this way, it is possible in particular to ensure that when the instrument is separated or withdrawn from the securing element it does not exert any force thereon which may change, undesirably and disadvantageously, the location or the position of the securing element in a bone part.

The instrument may be separated from the securing element in a particularly simple and reliable manner if the uncoupling device takes the form of a spreading device, for spreading a proximal end of the pulling part. For example, the pulling part may have pulling elements which are oriented in the proximal direction and which moreover may have a certain elasticity or flexibility, which enables the proximal ends of the pulling elements to be pivoted away from the longitudinal axis of the instrument and back towards it. In particular, the uncoupling device may be formed such that in the uncoupled position the proximal end of the pulling part completely frees the holding part and so enables the instrument to be released from the securing element without any force.

The instrument may be formed in a particularly simple manner if the pulling part takes the form of an outer sleeve and the pushing part comprises an inner sleeve that is assembled displaceably and/or pivotally in the outer sleeve. Optionally, the instrument may comprise an actuation device which is for moving the pushing part in relation to the pulling part and which is arranged or formed preferably at the distal end of the instrument. For example, the actuation device may comprise a rotary knob which may be screwed to the pulling part, for example by means of an external thread on the rotary knob and an internal thread, corresponding to this, at the distal end of the pulling part. Further, the rotary knob may be secured to the pushing part in the axial direction but be assembled such that it can rotate in relation thereto, such that as a whole, as a result of pivoting of the rotary knob, the pushing part is displaceable in relation to the pulling part, in the direction of the longitudinal axis. For a defined displacement movement, in particular corresponding guide elements may be provided which are arranged or formed on the pulling part and/or on the pushing part and which cooperate with one another.

According to a preferred embodiment of the invention, it may be provided for the pulling part to comprise at least one pulling part coupling element, for force- and/or positively-locking coupling to at least one correspondingly formed holding part coupling element of the holding part. In particular, the holding part coupling element may take the form of a cut or recess in the holding part, and the at least one pulling part coupling element may take the form of a corresponding projection having a retaining surface facing in the distal direction.

It is favorable if the at least one pulling part coupling element takes the form of a pulling part coupling projection that juts out in the direction of the longitudinal axis of the instrument. A pulling part coupling projection may for example engage in a corresponding recess in the holding part. Moreover, this construction of the pulling part coupling element makes it possible in a practical manner to grasp or take hold of the holding part from the outside, by the proximal end of the instrument, and conversely to free it again after it has been put in the final position in the bone part.

It is advantageous if the uncoupling device comprises at least one spreading member which may be moved from the coupled position to the uncoupled position and vice versa by relative movement of the pulling part and the pushing part parallel to the longitudinal axis. For example, the spreading member may take the form of one of the pulling elements described above, which protrude from the pulling part, oriented in the proximal direction.

Construction of the instrument is particularly simple and compact if the at least one spreading member is arranged or formed on the pulling part. As an alternative, it is also possible to provide the at least one spreading member on the pushing part.

According to a further preferred embodiment of the invention, it may be provided for the at least one spreading member to be movable from the coupled position, in which the at least one pulling part coupling element and the at least one holding part coupling element are in engagement, to the uncoupled position, in which the at least one pulling part coupling element and the at least one holding part coupling element are disengaged. In this way, it is possible in particular for two spreading members of this construction to embrace or substantially to embrace the holding part of the securing element, in order in this way to create a temporary connection between the instrument and the securing element.

The instrument may be formed in a particularly compact manner if the at least one spreading member carries or comprises the at least one pulling part coupling element. In particular, the at least one pulling part coupling element juts away from the spreading member, oriented in the direction of the longitudinal axis.

It is advantageous if, during the transfer from the coupled position to the uncoupled position, the at least one spreading member is movable away from a longitudinal axis of the instrument and, during the transfer from the uncoupled position to the coupled position, it is movable towards the longitudinal axis. In this way, the instrument may be temporarily coupled to the securing element and uncoupled from it again by a simple pivoting outward and inward movement of the spreading member.

Further, it is favorable if the spreading device comprises at least one spreading element that cooperates with the at least one spreading member and is arranged or formed on the pushing part. In particular if the at least one spreading member is arranged or formed on the pulling part, it is possible, as a result of the at least one spreading element that is arranged or formed on the pushing part, in cooperation with the at least one spreading member, for the instrument to be transferred from the coupled position to the uncoupled position and vice versa without the action of further external forces. In this way, the instrument can be released from the securing element simply and reliably and without any force.

The construction of the instrument is particularly simple if the at least one spreading element has or comprises a slide ramp face for the at least one spreading member, which is inclined in the distal direction and away from the longitudinal axis. In particular the slide ramp face may also cooperate with a projection on the spreading member, wherein the projection slides on the slide ramp face during transfer from the coupled position to the uncoupled position.

Further, it is advantageous if the instrument comprises a securing device for securing the instrument in the coupled position. In particular, with a securing device of this kind it is possible to connect the instrument to the securing element virtually non-detachably and temporarily inseparably. This is particularly advantageous because the instrument may be provided for example also for use in minimally invasive interventions and in this case it should also be possible to couple and uncouple it from a securing element without the operating personnel having direct sight of the operation site.

The securing device may be formed in a particularly simple manner constructional if it comprises at least one pulling part securing element and, cooperating with this, at least one pushing part securing element, and in the uncoupled position these are disengaged and in the coupled position they may be moved from an unsecured position in which they are disengaged to a secured position in which they are in engagement. In other words, when the instrument adopts the coupled position it may be secured therein, such that unintentional release or separation of the instrument from the securing element is not possible. For this purpose, when the instrument adopts the coupled position and is in particular coupled to a securing element, it is preferably transferred from the unsecured position to the secured position. In particular, the at least one pulling part securing element and the at least one pushing part securing element may be arranged and formed such that in the secured position they prevent the proximal end of the pulling part from spreading. However, in so doing it is also possible to prevent the instrument from being released from the securing element. In other words, in the secured position the instrument is securely coupled to the securing element.

It is advantageous if the at least one pulling part securing element takes the form of a pulling part securing projection or a pulling part securing recess, and if the at least one pushing part securing element takes the form of a pushing part securing recess that corresponds to the pulling part securing projection, or a pushing part securing projection that corresponds to the pulling part securing recess. In particular, the cooperating projections and recesses of the securing device may be arranged and formed such that in the secured position they prevent movement of the spreading member away from or towards the longitudinal axis. This can be achieved in particular if the recesses and projections mutually form abutments which act transversely in relation to the longitudinal axis, in particular radially. For example, they may be groove-shaped recesses that extend parallel to the longitudinal axis and projections that may be inserted therein parallel to the longitudinal axis.

It is favorable if the at least one pulling part securing element comprises a grooved block or is arranged or formed on a grooved block, and if the pushing part securing element comprises a guide recess or is arranged or formed on a guide recess. In particular, the grooved block may take the form of a projection having lateral grooves in which edges or projections of the guide recess that are directed towards one another can engage in the secured position. In particular, with a corresponding construction of grooves in a grooved block that are oriented away from one another, it is also possible in this way to achieve on both sides securing and guidance of the grooved block in the guide recess.

Advantageously, the guide recess comprises a guide portion and a securing portion, and the grooved block cooperates in the unsecured position with the guide portion and in the secured position with the securing portion. In this way, the guide recess may thus in particular have two portions, wherein the grooved block is merely guided in the guide portion but cannot prevent movement of the spreading member away from or towards the longitudinal axis. In particular in the secured position, the grooved block then cooperates with the securing portion such that for example only movement parallel to the longitudinal axis between the grooved block and the securing portion is possible but not movement of the grooved block away from or towards the longitudinal axis.

In order to limit movement of the pulling part and the pushing part in relation to one another, on the one hand, and at the same time to transfer the instrument from the coupled position to the uncoupled position and vice versa, on the other hand, it is favorable if the at least one spreading element proximally closes off the guide portion. In other words, in this way it is in particular possible to transfer the instrument from the coupled position to the uncoupled position when the pushing part adopts its most distal position in relation to the pulling part. This relative position between the pulling part and the pushing part may additionally also be predetermined by a further abutment which for example limits movement of the pushing part in the distal direction in relation to the pulling part.

Further, it may be favorable if the securing portion has at least one undercut which in the secured position is in engagement with the pulling part securing projection or the pulling part securing recess. The undercut may have the effect that movement of the pulling part or part thereof, for example the at least one spreading member, in a direction which is transverse in relation to the longitudinal axis, that is to say away from or towards the longitudinal axis, can be prevented in particular in a simple manner.

According to a further preferred embodiment of the invention, it may be provided for the instrument to be movable from the secured position into a locked position and vice versa and, in the locked position, for the pushing part to adopt its most proximal position in relation to the pulling part. The locked position may in particular be the position in which the pushing part of the instrument acts on a clamping device that is provided on the securing part in order to block temporarily relative movement between the holding part and the securing part, as described for example in DE 20 2011 051 211 U1 This allows the instrument to be used to fix temporarily a holding part which is movable in relation to the securing part about a centre of articulation, for example with a polyaxial screw in the assembled disposition. Thus, it is in particular possible in the locked position to lock the polyaxial nature of the securing element, so to speak, or in other words to block the securing element temporarily.

It is favorable if the pushing part has or comprises at least one pushing member for exerting a pushing force on a clamping device of the securing part, for temporarily blocking a relative movement of the securing part and the holding part in relation to one another in the locked position. For example, the at least one pushing member may take the form of one or more projections that are oriented in the proximal direction and are for example suitable for acting on contact points or engagement elements on a clamping element of the clamping device of the securing element.

According to a further preferred embodiment of the invention, it may be provided for the instrument to comprise a dismantling prevention device for temporarily securing the pushing part and the pulling part in relation to one another in an assembled disposition, in which the pulling part and the pushing part are non-detachably coupled to one another. In other words, the dismantling prevention device can in particular prevent the pulling part and the pushing part from being able to be inadvertently separated from one another during an operation by personnel using it. Further, the dismantling prevention device may favourably be formed such that only using an aid, for example an instrument formed specifically for this, can the at least one first dismantling prevention element and the at least one second dismantling prevention element be disengaged in order to take the instrument apart, that is to say in particular to separate the pulling part and the pushing part from one another for the purposes of cleaning and sterilisation.

It is particularly favorable if the dismantling prevention device comprises at least one first dismantling prevention element and at least one second dismantling prevention element that cooperates with the first dismantling prevention element, if the at least one first dismantling prevention element is arranged or formed on the pulling part, if the at least one second dismantling prevention element is arranged or formed on the pushing part, if the at least one first dismantling prevention element and the at least one second dismantling prevention element are in engagement or in contact with one another in the assembled disposition and are disengaged in a dismantled position in which the pulling part and the pushing part are separable from one another. In this way, it is possible in particular using minimal constructional work to ensure that the pulling part and the pushing part cannot be unintentionally separated from one another during an operation. Ideally, only two elements are required to construct the dismantling prevention device, namely a first dismantling prevention element on the pulling part and a second on the pushing part.

It is advantageous if the at least one first dismantling prevention element and the at least one second dismantling prevention element are only in contact or in engagement with one another in the assembled disposition when the instrument adopts the uncoupled position. In this way, it is possible to define the uncoupled position at the same time. In particular, it is possible in this way to limit for example a maximum spread of the spreading members of the pulling part in order to avoid damaging the instrument.

Construction of the dismantling prevention device is particularly simple if the at least one first or the at least one second dismantling prevention element takes the form of a projection pointing radially away from the longitudinal axis, and the respectively other dismantling prevention element takes the form of an abutment having an abutment surface facing in the distal direction. This construction in particular makes it possible to limit movement of the pulling part and the pushing part towards one another in the dismantled position. In other words, a most distal position of the pushing part in relation to the pulling part can thus be defined.

In order to simplify joining the pulling part and the pushing part in order to construct the instrument, it is favorable if the projection that is oriented radially away from the longitudinal axis is assembled or held such that it is radially movable. For example, pivoting inward or outward, towards or away from the longitudinal axis, allows it to be moved out of engagement or contact with the abutment in order in this way to allow the pulling part and the pushing part to be separated from one another.

The instrument becomes particularly simple and intuitive to handle if the dismantling prevention device takes the form of a latching and/or snap-fitting connection device, with first and second latching and/or snap-fitting members, which are arranged or formed in one case on the pushing part and in the other on the pulling part, in engagement or contact in the assembled disposition. A latching and/or snap-fitting connection device makes it possible to join the pulling part and the pushing part, in particular by pushing the pushing part into the pulling part until the first and second latching and/or snap-fitting members are in engagement or in contact with one another, such that unintentional separation of the pulling part and the pushing part from one another can be prevented.

In order to improve handling of the instrument, it is advantageous if the dismantling prevention device is arranged or formed in the region of a distal end of the instrument. In this way, it is decidedly unlikely that the dismantling prevention device can come into contact with body tissue that in some circumstances could become trapped in the region of the dismantling prevention device or injured. For this reason, no particular safety measures have to be taken here to prevent the possibility of body tissue being damaged by the dismantling prevention device when the instrument is used.

The present invention relates to a vertebral column stabilization system comprising at least two surgical securing elements and at least one connection element, wherein at least one of the at least two surgical securing elements comprises a securing part, a holding part with a connection element seating, and a fixing element which is fixable to the holding part, for fixing the connection element in the connection element seating, further comprising a medical instrument for holding and handling at least one of the surgical securing elements, which comprises a securing part and a holding part, which is assembled such that in an assembled disposition it is movable in relation to the securing part, for a connection element, wherein the instrument has a proximal and a distal end, defines a longitudinal axis and comprises a pulling part and, movable in relation to the latter in the direction of the longitudinal axis, a pushing part, wherein the proximal end is temporarily couplable to the securing element in the assembled disposition, further comprising an uncoupling device for actively transferring the instrument from a coupled position, in which the pulling part and the holding part are coupled, to an uncoupled position, in which the pulling part and the holding part are separable from one another.

A vertebral column stabilization system having one of the advantageous medical instruments described above for holding and handling at least one of the surgical securing elements also has in particular the advantages that have been described above in the context of preferred embodiments of the instruments. It is in particular possible using these medical instruments to implant securing elements for the vertebral column stabilization system in a simple and reliable manner. The securing part may for example take the form of any bone anchor, in particular the form of a shaft provided with an external thread. The holding part may take any form that is suitable for receiving rod- or plate-shaped connection elements in order in this way to keep mutually coupled securing elements of the vertebral column stabilization system at a predetermined spacing from one another.

It is advantageous if the securing part and the holding part are held such that they are movable in relation to one another in an assembled disposition. This makes it possible to orient the holding part relative to the securing part such that the connection element seating is oriented in optimum manner for receiving a connection element. In other words, it is possible in this way for longitudinal axes of the securing part and the holding part to be tilted in relation to one another and oriented as desired in order on the one hand to ensure optimum anchoring of the securing part on a patient's bone part and on the other hand to orient and arrange the connection element in optimum manner. Of course, as an alternative it is also possible to use securing elements which have a securing part and a holding part that are not movable in relation to one another. In particular, it is also possible to provide securing elements which are formed entirely in one piece and whereof the holding and securing parts are not movable in relation to one another.

According to a further preferred embodiment of the invention, it may be provided for the at least one securing element to comprise at least one clamping member which, in the assembled disposition, is held movably on the holding part and, in an implantation position, is held in clamping manner between the connection element and the securing part. The clamping member may in particular be part of a clamping device for the securing element and serve to restrict, in part or entirely, mobility between the holding part and the securing part. In particular, it may make it possible for a clamping member of this kind, using one of the advantageous medical instruments described above, to block mobility of the holding part and the securing part in relation to one another, for example by the pushing part exerting a pushing force on the clamping member, with the result that the clamping member is pressed against the securing element, for example against a spherical head thereof, as a result of which the securing element is locked if clamping forces are sufficiently great, for example the holding part and the securing part of the securing element that takes the form of a polyaxial screw being locked.

FIG. 1 illustrates schematically a vertebral column stabilization system designated by the reference numeral 10. It comprises at least two surgical securing elements 12, at least one connection element 14 and at least one medical instrument 16 for holding and handling at least one of the securing elements 12. As an option, the vertebral column stabilization system may also comprise a holding instrument 18 for holding and handling the connection element 14.

The securing element 12 may in particular take the form of a polyaxial screw 20 which comprises a securing part 22 and a holding part 24. A distal end of the securing part 22 takes the form of a spherical head 26 which is seated in a corresponding seating 28 in the holding part 24. The securing part 22 has an elongate shaft 30, which is provided with an external thread 32 that preferably takes the form of a self-cutting bone screw in order to be able to screw the securing part 22 into a bone part, for example a pedicle of a vertebra 34 of a vertebral column 36 of a patient. As an option, the shaft 30 may be cannulated, that is to say may comprise a longitudinal bore 38 that extends proximally from a tool seating 40 in the head 26 as far as a proximal end 42 of the shaft.

The holding part 24 as a whole is formed to be substantially sleeve-shaped and comprises a connection element seating 44 which is open in the distal direction and into which a rod- or plate-shaped connection element 14 may be inserted with its longitudinal axis 46 transverse in relation to a longitudinal axis 48 of the holding part 24. For fixing the connection element 14 in the connection element seating 44 there serves a fixing element 50, in particular in the form of a grub screw which has an external thread 54 that is formed to correspond to an internal thread 56 on the holding part 24.

A clamping member 58 in the form of a sleeve is inserted into the holding part 24 from the distal direction and comprises at the proximal end a clamping face 60 that is in the shape of a hollow sphere, is formed to correspond to the spherical head 26 and abuts against the latter. Facing in the opposite direction, there is further formed on the clamping member 58 an abutment surface 62 in the shape of a hollow cylinder, for the preferably rod-shaped connection element 40, which has a circular or substantially circular cross section. In an implantation position, which is illustrated schematically in FIG. 1, the fixing element 50 is screwed into the holding part 24 from the distal direction and presses directly against the connection element 14, which is inserted into the connection element seating 44 and in turn presses the clamping member 58 of a clamping device (designated overall by the reference numeral 64) of the securing element 12 against the securing part 22, namely the head 26 thereof, such that the latter is clamped in the seating 28. In this way, the polyaxial screw 20 can be blocked or locked in the desired manner, such that the securing part 22 and the holding part 24 can have their longitudinal axes aligned with one another and be fixed in relation to one another, temporarily or permanently.

The instrument 16 serves for holding and handling the securing element 12. In the exemplary embodiments illustrated in the Figures, it comprises three parts, namely a pulling part 66 that takes the form of an outer sleeve 174, a pushing part 68, and an actuation element 70. The pulling part 66, the pushing part 68 and the actuation element 70, in the form of a rotary knob 72, are all formed to be in the form of a sleeve or substantially in the form of a sleeve, and are described in detail below.

The pulling part 66 comprises a sleeve portion 74 that extends over approximately a third of a total length of the pulling part 66 and from which there extend away in the proximal direction two spreading members 76 in the form of arms. Overall, the pulling part 66 is formed to be mirror-symmetrical about a plane containing the longitudinal axis 78. From the distal end 80 of the pulling part 66 there extends in the proximal direction an internally threaded portion 82. Two window-like apertures 84 that extend substantially in the longitudinal direction are formed diametrically opposite each other in relation to the longitudinal axis 78 and extend partly into the internally threaded portion 82. They form part of a dismantling prevention device designated overall by the reference 86. An arm member 88 oriented in the proximal direction and having an end surface 90 facing in the proximal direction protrudes from a distal end of the aperture 84 and forms an abutment 92 for a projection 94 on the pushing part 68. The abutment 92 forms a first dismantling prevention element 96 and the projection 94 forms a second dismantling prevention element 98, and the function of these will be described below in detail.

Proximal of the apertures 84 there is formed on the sleeve portion 74 a polygonal portion 100 having planar surface regions that face radially away from the longitudinal axis 78.

Adjoining a proximal end 102 of the spreading member 76 there is a pulling part coupling element 104 which projects in the direction of the longitudinal axis 78 and takes the form of a pulling part coupling projection 176, to correspond to a holding part coupling element 106 on the holding part 24. The holding part coupling element 106 takes the form of a recess in the holding part 24, oriented away from the longitudinal axis 78 and having a retaining face 108, oriented in the proximal direction, for a latching face 110 of the pulling part coupling element 104 that is oriented in the distal direction. On the proximal side, the side face 112 oriented in the direction of the longitudinal axis 78 is slightly sloped and forms a slide ramp face 114 which simplifies engagement with the holding part 24.

Somewhat further towards the distal side of the pulling part coupling element 104, a retaining member 116 protrudes from the spreading member 76 in the direction oriented towards the longitudinal axis 78 and abuts against a distal end 118 of the holding part 24 when the instrument 16 and the securing element 12 adopt the coupled position.

Even further towards the distal side than the retaining member 116, there is formed on the spreading member 76 a projection, oriented in the direction of the longitudinal axis 78, in the form of a T-shaped grooved block 120. The latter is formed to be substantially cuboidal and has two grooves 122 which run parallel to the longitudinal axis and face away from one another. It forms a pulling part securing element 124 of a securing device 126 designated overall by the reference 126 for securing the instrument 16 in the coupled position.

The spreading members 76 have sufficient elasticity for proximal ends thereof to be able to pivot outward, away from the longitudinal axis 78, when the pulling part coupling elements 104 are pushed up onto sloped guide faces 128 of the holding part 24 and to snap back in the direction thereof as soon as the latching face 110 can reach behind the retaining face 108.

Starting from a proximal end, the actuation element 70 has an externally threaded portion 130 which is formed to correspond to the internally threaded portion 82. This makes it possible to screw the rotary knob 72 into the pulling part 66 from the distal end. Starting from a distal end, a polygon 132 having planar surface regions that face away from the longitudinal axis 78 is formed on an outer side of the actuation element.

Oriented in the proximal direction, a plurality of latching members 134 of a latching connection 136 that are distributed over the periphery protrude from the proximal end of the actuation element 70 and can cooperate with a latching member 138, in the form of an annular flange directed radially away from the longitudinal axis 78, on the pushing part 68. By snap-fitting the actuation element 70 onto a distal end of the pushing part 68, an axially secured connection is made between the actuation element 70 and the pushing part 68, this latching connection 136 nonetheless enabling the actuation element 70 and the pushing part 68 to pivot in relation to one another.

Somewhat further towards the proximal end of the latching member 138, on an outer side of the pushing part 68, there are formed the two projections 94, which are diametrically opposite one another in relation to the longitudinal axis 78. In the peripheral direction, the projections 94 are dimensioned such that they may be guided in the apertures 84 parallel to the longitudinal axis 78.

The construction of a proximal end or a proximal end region of the pushing part 68 is described below in more detail, in particular as regards functioning of the instrument 16. Starting from its proximal end, the pushing part 68 has two pushing part portions 142 which are separated by slits 140 and each carry two pushing members 144 in the form of rods oriented in the distal direction. Free ends 146 of the pushing members 144 are formed such that they may penetrate recesses 148 in the clamping member 58. The recesses 148 are positioned adjacent to the abutment face 62, so that the connection element 14 can still be introduced into the connection element seating 44 when the ends 146 of the pushing members 144 penetrate the recess at 148.

Further, a guide recess 150 extending parallel to the longitudinal axis is made on each pushing part portion 142. As illustrated for example in FIG. 4b, this is aligned with the projections 94. Each guide recess 150 has a guide portion 152 and a securing portion 154. Both are of approximately the same length, the guide portion 152 being somewhat wider than the securing portion 154. The securing portion 154 moreover has a somewhat reduced wall thickness. A width of the securing portion 154 is dimensioned such that the T-shaped grooved slot, which is freely displaceable in the guide portion 152 in the longitudinal direction, can cooperate with the projections 156 that narrow the securing portion 154 on both sides and which delimit an undercut in the securing portion 154, in that the projections 156 can engage in the grooves 122. The projections 156 thus form pushing part securing elements 158 which cooperate with the pushing part securing elements 124 in the secured position of the instrument 16.

A proximal end of the pushing part portion 142 forms a spreading element 160 which closes off the guide recess 150 transversely in relation to the longitudinal axis 78. In cooperation with the pulling part securing element 124 and the spreading members 76, it forms an uncoupling device 162 in the form of a spreading device 172 for transferring the instrument 16 from the coupled position, in which the pulling part 66 and the holding part 24 are coupled, to an uncoupled position, in which the pulling part 66 and the holding part 24 are separable from one another. The spreading element 160 has two slide ramp faces 164 and 166, wherein the slide ramp face 164 faces substantially in the distal direction and the slide ramp face 166 faces substantially in the proximal direction.

Mounting of the instrument 16 and functioning thereof in cooperation with the securing element 12 are described below.

For preparation and mounting of the instrument 16, in a first step the actuation element 70 is coupled to the pushing part 168, which forms an inner sleeve 168, by snap-fitting the actuation element 70 onto the distal end of the pushing part 68.

In a next step, the pushing part 68 is now pushed from the distal direction, proximal end first, into the distal end of the pulling part 66 until the externally threaded portion 130 and the internally threaded portion 82 come into engagement with one another. Rotation of the rotary knob 72 now causes the actuation element 70 to be screwed into the pulling part 66 until the second dismantling prevention element 98 is snap-fitted into the aperture 84. The aperture 84 is dimensioned in its width and longitudinal direction such that as a result of rotation of the rotary knob 72 the pushing part 68 can be displaced in relation to the pulling part 66 but is at the same time guided axially. Movement of the pushing part 68 in the distal direction relative to the pulling part 66 is limited by the abutment 92, against which the distal end of the second dismantling prevention element 98 abuts. This is the case when the instrument 16 adopts the uncoupled position, described below.

As soon as the dismantling prevention device 86, which is formed as a latching and/or snap-fitting connection device, snaps in, the T-shaped grooved block 120 slides onto the slide ramp face 164, such that the spreading members 76 are spread outward, away from the longitudinal axis 78. In this uncoupled position, it is possible to push the proximal end of the instrument 16 over the holding part 24 of the securing element 12 without exerting force on the securing element 12.

If the rotary knob 72 is turned further clockwise, the pushing part 78 moves further in the proximal direction relative to the pulling part 66, whereupon the spreading members 76 can yield in the direction of the longitudinal axis 78 again. Once the proximal end of the pulling part 66 is pushed over a holding part 24, the pulling part coupling elements 104 can engage in the holding part coupling elements 106, such that the instrument 16 is temporarily coupled to the actuation element 12.

If the pushing part 68 is displaced further in the proximal direction relative to the pulling part 66 as a result of turning the rotary knob 72 clockwise, the T-shaped grooved block 120 first moves in the guide portion 152 of the guide recess 150. While the T-shaped grooved block 120 is entirely in the region of the guide portion 152, the spreading members 76 can pivot radially away from the longitudinal axis 78. In this relative position, the so-called unsecured position, of the pushing part 68 and the pulling part 66 in relation to one another, it is also possible to push the instrument 16 onto the holding part 24 of the securing element 12. During this coupling procedure, the pulling part coupling elements 104 slide on the guide faces 128 of the holding part 24 until the latching face 110 engages behind the retaining face 108, and then the spreading member 76 can snap back in the direction of the longitudinal axis 78.

The pushing part 68 can be moved even further in the proximal direction in relation to the pulling part 66 by pivoting the rotary knob 72 clockwise. As soon as the T-shaped grooved block 120 reaches the region of the securing portion 154, the projections 156 engage in the grooves 122. The pushing part securing elements 158 and pulling part securing elements 124 are now in engagement and prevent the spreading members 76 from moving away from the longitudinal axis 78. The instrument 16 now adopts the secured position.

Finally, if the rotary knob 72 is turned further clockwise, the instrument 16 can be transferred to the locked position. In this position, the pushing part 68 adopts its most proximal position in relation to the pulling part 66. Once the instrument 16 is coupled to the securing element 12, in the locked position the ends 146 penetrate the recesses 148, so the clamping member 58 of the clamping device 64 is pressed towards the head 26. Since the pulling part 66, which is coupled to the holding part 24, exerts a pulling force on the securing element 12 in the opposite direction, this activation of the clamping device 64 locks the holding part 24 relative to the securing part 22. The securing element 12 as a whole is now rigid and the holding part 24 is held immovably, clamped against the securing part 22.

It is now possible, for example with the holding instrument 18, to introduce a connection element 14 into the connection element seatings 44 of two securing elements 12 that have been implanted in adjacent vertebrae 34, as illustrated schematically in FIG. 1. The fixing elements 50 can be applied using instruments that are not illustrated and can be screwed to the respective holding part 24 in order finally to fix the connection element 14 to the securing elements 12.

Once the connection element 14 has been fixed to the securing element 12, the instrument 16 may be released from the holding part 24 again. For this purpose, the rotary knob 72 is pivoted anticlockwise until the T-shaped grooved block 120 slides on the spreading element 160 again, as a result of which the spreading members 76 are pivoted radially away from the longitudinal axis 78. In this uncoupled position, the abutment 92 abuts with its end face 70 against a distal end face of projection 94. Hence, the dismantling prevention device 86 prevents the pushing part 68 from being able to be unintentionally unscrewed from the pulling part 66. Release of the dismantling prevention device 86 is only possible using an instrument or tool provided specially therefor. Unintentional separation of the pushing part 68 from the pulling part 66 during an operation is thus impossible.

The instrument 16, which is in the uncoupled position, can now be withdrawn from the holding part 24 in the distal direction, since the pulling part coupling element 104 frees the holding part coupling element 106.

The invention claimed is:

1. A medical instrument for holding and handling a surgical securing element, which comprises a securing part and a holding part, which is assembled such that in an assembled disposition it is movable in relation to the securing part, for a connection element, wherein the instrument has a proximal and a distal end, defines a longitudinal axis and comprises a pulling part and, movable in relation to the latter in the direction of the longitudinal axis, a pushing part, wherein the proximal end is temporarily couplable to the securing element in the assembled disposition, further comprising an uncoupling device for actively transferring the instrument from a coupled position, in which the pulling part and the holding part are coupled, to an uncoupled position, in which the pulling part and the holding part are separable from one another, wherein the uncoupling device takes the form of a spreading device, for spreading a proximal end of the pulling part.

2. A medical instrument according to claim 1, wherein the pulling part takes the form of an outer sleeve, and wherein the pushing part comprises an inner sleeve that is assembled at least one of displaceably and pivotally in the outer sleeve.

3. A medical instrument according to claim 1, wherein the pulling part comprises at least one pulling part coupling element, for at least one of force- and positively-locking coupling to at least one correspondingly formed holding part coupling element of the holding part.

4. A medical instrument according to claim 3, wherein the at least one pulling part coupling element takes the form of a pulling part coupling projection that juts out in the direction of the longitudinal axis of the instrument.

5. A medical instrument according to claim 1, wherein the uncoupling device comprises at least one spreading member which is movable from the coupled position to the uncoupled position and vice versa by relative movement of the pulling part and the pushing part parallel to the longitudinal axis.

6. A medical instrument according to claim 5, wherein the at least one spreading member is arranged or formed on the pulling part.

7. A medical instrument according to claim 5, wherein the at least one spreading member is movable from the coupled position, in which the at least one pulling part coupling element and the at least one holding part coupling element are in engagement, to the uncoupled position, in which the at least one pulling part coupling element and the at least one holding part coupling element are disengaged.

8. A medical instrument according to claim 1, characterised by a securing device for securing the instrument in the coupled position.

9. A medical instrument according to claim 8, wherein the securing device comprises at least one pulling part securing element and, cooperating with this, at least one pushing part securing element, and in the uncoupled position these are disengaged and in the coupled position they are movable from an unsecured position in which they are disengaged to a secured position in which they are in engagement.

10. A medical instrument according to claim 9, wherein the at least one pulling part securing element takes the form of a pulling part securing projection or a pulling part securing recess, and wherein the at least one pushing part securing element takes the form of a pushing part securing recess that corresponds to the pulling part securing projection, or a pushing part securing projection that corresponds to the pulling part securing recess.

11. A medical instrument according to claim 9, wherein the at least one pulling part securing element comprises a grooved block or is arranged or formed on a grooved block, and wherein the pushing part securing element comprises a guide recess or is arranged or formed on a guide recess.

12. A medical instrument according to claim 11, wherein the guide recess comprises a guide portion and a securing portion, and wherein the grooved block cooperates in the unsecured position with the guide portion and in the secured position with the securing portion.

13. A medical instrument according to claim 12, wherein the at least one spreading element proximally closes off the guide portion.

14. A medical instrument according to claim 1, characterised by a dismantling prevention device for temporarily securing the pushing part and the pulling part in relation to one another, in an assembled disposition in which the pulling part and the pushing part are non-detachably coupled to one another.

15. A medical instrument according to claim 14, wherein the dismantling prevention device comprises at least one first dismantling prevention element and at least one second dismantling prevention element that cooperates with the first dismantling prevention element, wherein the at least one first dismantling prevention element is arranged or formed on the pulling part, wherein the at least one second dismantling prevention element is arranged or formed on the pushing part, wherein the at least one first dismantling prevention element and the at least one second dismantling prevention element are in engagement or in contact with one another in the assembled disposition and are disengaged in a dismantled position in which the pulling part and the pushing part are separable from one another.

16. A vertebral column stabilisation system comprising at least two surgical securing elements and at least one connection element, wherein at least one of the at least two surgical securing elements comprises a securing part, a holding part with a connection element seating, and a fixing element which is fixable to the holding part, for fixing the connection element in the connection element seating, further comprising a medical instrument for holding and handling at least one of the surgical securing elements, which comprises a securing part and a holding part, which is assembled such that in an assembled disposition it is movable in relation to the securing part, for a connection element, wherein the instrument has a proximal and a distal end, defines a longitudinal axis and comprises a pulling part and, movable in relation to the latter in the direction of the longitudinal axis, a pushing part, wherein the proximal end is temporarily couplable to the securing element in the assembled disposition, further comprising an uncoupling device for actively transferring the instrument from a coupled position, in which the pulling part and the holding part are coupled, to an uncoupled position, in which the pulling part and the holding part are separable from one another, wherein the uncoupling device takes the form of a spreading device, for spreading a proximal end of the pulling part.

17. A vertebral column stabilisation system according to claim 16, wherein the securing part and the holding part are held movable in relation to one another in an assembled disposition.

18. A vertebral column stabilisation system according to claim 17, wherein the at least one securing element comprises at least one clamping member which, in the assembled disposition, is held movably on the holding part and, in an implantation position, is held in clamping manner between the connection element and the securing part.

* * * * *